United States Patent
Jung et al.

(10) Patent No.: US 11,105,788 B2
(45) Date of Patent: Aug. 31, 2021

(54) APPARATUS FOR DETECTING INTERNAL DEFECT IN TRANSFORMER

(71) Applicant: HYOSUNG HEAVY INDUSTRIES CORPORATION, Seoul (KR)

(72) Inventors: Jae Ryong Jung, Gimhae-si (KR); Young Min Kim, Gimhae-si (KR); Sung Wook Kim, Changwon-si (KR); Hyang Eun Jo, Changwon-si (KR)

(73) Assignee: HYOSUNG HEAVY INDUSTRIES CORPORATION, Seoul (KR)

( * ) Notice: Subject to any disclaimer, the term of this patent is extended or adjusted under 35 U.S.C. 154(b) by 107 days.

(21) Appl. No.: 16/473,519

(22) PCT Filed: Dec. 5, 2017

(86) PCT No.: PCT/KR2017/014160
§ 371 (c)(1),
(2) Date: Jun. 25, 2019

(87) PCT Pub. No.: WO2018/124518
PCT Pub. Date: Jul. 5, 2018

(65) Prior Publication Data
US 2020/0103391 A1    Apr. 2, 2020

(30) Foreign Application Priority Data
Dec. 26, 2016  (KR) .......................... 10-2016-0179552

(51) Int. Cl.
*G01N 33/28* (2006.01)
*G01R 31/62* (2020.01)

(52) U.S. Cl.
CPC ......... *G01N 33/2841* (2013.01); *G01R 31/62* (2020.01)

(58) Field of Classification Search
CPC ........................... G01N 33/2841; G01R 31/62
See application file for complete search history.

(56) References Cited

U.S. PATENT DOCUMENTS 8,616,045 B2 * 12/2013 Cavallini ........... G01N 33/2841
                                                              73/19.11
9,234,834 B2 *  1/2016 Van Mechelen ....... G01N 21/81
(Continued)

FOREIGN PATENT DOCUMENTS

KR    10-2006-0092648 A    8/2006
KR    10-2008-0067484 A    7/2008
(Continued)

*Primary Examiner* — Reena Aurora
(74) *Attorney, Agent, or Firm* — Novick, Kim & Lee, PLLC; Jae Youn Kim (57) ABSTRACT

An apparatus for detecting internal defects in a transformer is provided. The apparatus detecting internal defects that arise in the interior by integrating an electrode for electrically detecting defects and a sensor for detecting internal gas into a single body and inserting same into the interior. The apparatus for detecting internal defects in a transformer according to the present invention comprises: a metal member of a set length; a plurality of electrodes, disposed around the metal member, for detecting electrical signals generated due to internal defects of the transformer; an insulating member formed so as to contain the metal member and plurality of electrodes; and a gas sensor, installed at the end of the metal member, for detecting gas inside the transformer.

15 Claims, 5 Drawing Sheets

(56) References Cited

U.S. PATENT DOCUMENTS

| | | | |
|---|---|---|---|
| 9,766,283 B2* | 9/2017 | Han | ................. G01R 31/62 |
| 9,884,269 B2* | 2/2018 | Hunter | ............. B01D 19/0031 |
| 2012/0286764 A1 | 11/2012 | Lyu et al. | |

FOREIGN PATENT DOCUMENTS

| | | |
|---|---|---|
| KR | 10-1251876 B1 | 4/2013 |
| KR | 10-1264548 B1 | 5/2013 |
| KR | 10-1486995 B1 | 1/2015 |

* cited by examiner

APPARATUS FOR DETECTING INTERNAL DEFECT IN TRANSFORMER

TECHNICAL FIELD

The present invention relates to an apparatus for detecting internal defects in a transformer and, more particularly, to an apparatus for detecting internal defects in a transformer, the apparatus detecting the internal defects occurring inside the transformer by allowing an electrode for detecting an electrical fault and a sensor for detecting internal gas to be integrally provided and the same to be inserted into the transformer.

BACKGROUND ART

Various methods for detecting internal defects in a transformer have been proposed. For example, there are a method of measuring an abnormal signal by installing an ultrasonic sensor in a transformer enclosure, a method of obtaining an abnormal signal by inserting a ultra high frequency (UHF) electromagnetic wave sensor into a drain valve of a transformer, a method of regularly analyzing the dissolved gas from remote by extracting the insulating oil in the transformer, and a method of applying a gas analyzer capable of detecting hydrogen or moisture to a transformer.

However, the method of attaching the ultrasonic sensor to the transformer enclosure is not suitable for on-line monitoring due to high influence of the external noise and low sensor sensitivity during operation. The UHF electromagnetic wave sensor inserted into the drain valve is suitable for on-line monitoring due to less influence of external noise and high sensor sensitivity, but there is a problem that the UHF electromagnetic wave sensor cannot detect thermal faults.

Korean Patent Nos. 1095778 and 1264548 disclose a partial discharge detection apparatus in which a sensing part is inserted into the hollow space of a drain valve and a space inside a transformer to generate a partial discharge signal in a transformer. However, in the documents disclosed above, only faults due to the partial discharge are detected, and thermal faults cannot be detected.

Also, Korean Patent No. 1486995 discloses a transformer fault detection apparatus in which a plurality of sensors is integrally mounted on a drain valve in a transformer to sense signals, thereby accurately estimating the position of a partial discharge generation source in a transformer. The above-mentioned document in the related art is provided with an integrated sensor including an ultrasonic sensor, an electromagnetic wave sensor, a gas sensor, and a temperature sensor to detect electrical and thermal faults, but there is a problem that detection sensitivity of the electromagnetic wave sensor decreases since the internal structure is complicated and the propagation path of the electromagnetic wave generated during partial discharge is affected depending on the position between the sensors.

DISCLOSURE

Technical Problem

Accordingly, the present invention has been made keeping in mind the above problems occurring in the related art, and an object of the present invention is to provide an apparatus for detecting internal defects in a transformer, the apparatus detecting the internal defects of the transformer by allowing a sensor for detecting an electrical fault and a sensor for detecting internal gas to be integrally provided.

It is another object of the present invention to provide an apparatus for detecting internal defects in a transformer, which is capable of reducing a reflection loss at an electrode for detecting partial discharge, thereby improving the performance and reliability of fault detection.

It is still another object of the present invention to provide an apparatus for detecting internal defects in a transformer, which allows a gas sensor for detecting internal gas of a transformer to be provided at a position that does not affect electrodes that detect electromagnetic waves caused due to the internal defects.

Technical Solution

An apparatus for detecting internal defects in a transformer according to the present invention includes a metal member having a predetermined length; a plurality of electrodes provided around the metal member to detect electric signals generated due to the internal defects of the transformer; and an insulating member formed so as to include the metal member and the plurality of electrodes.

A first electrode of the plurality of electrodes may be provided to be in contact with an end of the metal member.

Remaining second electrodes except the first electrodes of the plurality of electrodes may be connected to the first electrode to be provided in parallel to the metal member.

The second electrodes may be each implemented in a shape of a plate having a predetermined area.

The metal member may have a cylindrical shape, and the second electrodes may be each disposed such that inner surfaces thereof are parallel to an outer surface of the cylindrical metal member while having a predetermined area.

The second electrodes each may have a length, an area, and a shape different from each other.

The second electrodes may be provided at a distance at which mutual coupling of each with the metal member occurs.

The second electrodes each may generate resonance different from the metal member.

The transformer internal defect detection apparatus may further include a gas sensor provided at an end of the metal member to detect gas dissolved in insulating oil inside the transformer.

The gas sensor may be provided at the end of the metal member so as to be exposed to the outside of the insulating member.

The gas sensor may be provided at a position at which an effect on an electrical signal received by the plurality of electrodes is minimized The gas sensor may include a hydrogen detection sensor for detecting hydrogen gas of the dissolved oil inside the transformer.

The metal member, the plurality of electrodes, the insulating member, and the gas sensor may be integrally combined to constitute a sensor head unit, and the sensor head unit may be connected to an end of an insulation support having a predetermined length and thus inserted into the transformer from an outside of the transformer by the insulating support.

The transformer internal defect detection apparatus may further include an analyzer receiving signals detected by the plurality of electrodes and the gas sensor to analyze the internal defects of the transformer.

Advantageous Effects

According to the present invention, electrical defects and thermal defects occurring inside the transformer can be simultaneously detected.

Further, according to the present invention, there is an effect of reducing a reflection loss in the electrode for detecting the partial discharge, which is an electrical defect occurring in the transformer, thereby improving the reliability of detection of the partial discharge defect.

According to the present invention, when the partial discharge sensor and the gas sensor are provided, the gas sensor is provided at a position that does not affect the partial discharge sensor for detecting electromagnetic waves generated by partial discharge inside the transformer, so that the gas sensor does not affect the detection performance of the partial discharge sensor.

MODE FOR INVENTION

Hereinafter, some embodiments of the present invention will be described in detail with reference to exemplary drawings. It is to be noted that, in adding reference numerals to the constituent elements of the drawings, the same constituent elements are denoted by the same reference numerals whenever possible, even when they are shown in different drawings. In the following description of the embodiments of the present invention, when it is determined that a detailed description of known functions and configurations incorporated herein hinders understanding for the embodiments of the present invention, the detailed description will be omitted.

In describing the components of the embodiment of the present invention, terms such as first, second, A, B, (a), and (b) can be used. These terms are intended to distinguish the constituent elements from other constituent elements, and the terms do not limit the nature, order or order of the constituent elements. When a constituent element is described as being "linked", "coupled", or "connected" to another constituent element, it will be appreciated that they can be directly coupled or connected, and also they can be "linked", "coupled", or "connected" with still another constituent element in between.

Figure 1:
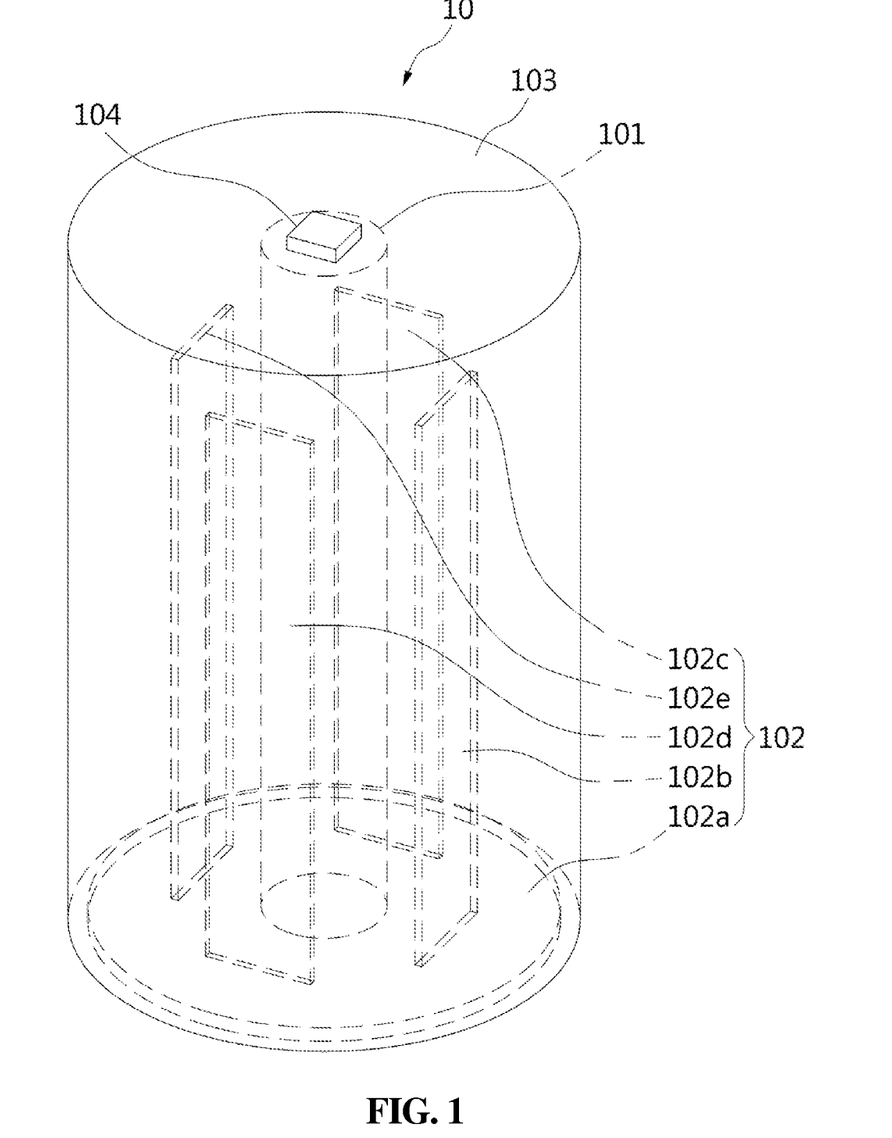
FIG. 1 is a configuration diagram showing an apparatus for detecting internal defects in a transformer (hereinafter, referring to "transformer internal defect detection apparatus") according to an embodiment of the present invention.

FIG. 1 is a block diagram showing a transformer internal defect detection apparatus according to an embodiment of the present invention.

Referring to FIG. 1, a transformer internal defect detection apparatus 100 according to the present invention is configured to include a metal member 101 having a predetermined length, a plurality of electrodes 102 provided around the metal member 101, and an insulating member 103 including the metal member 101 and the plurality of electrodes 102.

The metal member 101 and the plurality of electrodes 102 are formed inside the insulating member 103, and preferably have a shape that is inserted and molded into the insulating member 103.

For example, after the plurality of electrodes 102 is disposed around the metal member 101 having a predetermined length, the insulating member 103 is processed to be molded in such a manner to surround the metal member 101 and the plurality of electrodes 102 from the outside.

Due to such insulating member 103, the metal member 101 and the electrode 102 are shut off from the outside and shut off from contact with insulating oil inside the transformer 10.

In this embodiment, the metal member 101 may be formed in a cylindrical shape, while, in another embodiment, the metal member 101 may be formed in a polygonal shape.

The plurality of electrodes 102 is configured to detect an electrical signal generated due to internal defects of the transformer 10. In particular, when the transformer internal defect detection apparatus 100 according to the present invention is inserted into the transformer 10, the plurality of electrodes 102 detects an electrical signal transmitted at the occurrence of the internal defects.

For example, when a partial discharge (PD) occurs inside the transformer 10, the electromagnetic wave due to the partial discharge is transmitted through the insulating oil to reach the plurality of electrodes 102 and an electric signal corresponding to the electromagnetic wave is output through a cable connected to each electrode 102.

A first electrode 102a which is one of the plurality of electrodes 102 is provided to be in contact with one end of the metal member 101 and the other second electrodes 102b to 102e except for the first electrode 102a are connected to the first electrode 102a to be provided in parallel with the metal member 101.

Although the four second electrodes 102b to 102e are shown for convenience of illustration in the drawing, the present invention is not limited thereto, and the number of the second electrodes 102b to 102e may be one or more, preferably one to six.

For example, the other second electrodes 102b to 102e may be implemented in the form of a plate having the same length and area as each other. As another example, the second electrodes 102b to 102e may be implemented in the form of plates having lengths and areas different from each other. The plate-shaped second electrodes 102b to 102e are arranged in parallel with the metal member 101, each being provided in the form of a plate with the same length or different lengths.

As another example, when the metal member 101 is provided in a cylindrical shape, the other second electrodes 102b to 102e may be provided so that internal surfaces thereof are disposed in parallel with the external surface of the cylindrical metal member 101, each having the same length and area as each other or different lengths and areas from each other. More specifically, the inner surfaces of the second electrodes 102b to 102e have the same curvature as the outer surface of the cylindrical metal member 101 and thus are disposed in parallel with the outer surface of the metal member 101.

Herein, the installation positions of the second electrodes 102b to 102e are important. In other words, it is important to determine how far the second electrodes 102b to 102e are located from the metal member 101. In the present invention, it is preferable that the respective second electrodes 102b to 102e are provided at a distance in which mutual coupling with the metal member 101 occurs.

Such mutual coupling is a phenomenon in which electrical energy is transmitted between the second electrodes 102b to 102e and the metal member 101, in which capacitance is present between the metal member 101 and each of the second electrodes 102b to 102e so that a signal is transmitted even at a position spaced apart from each other. Thus, the mutual coupling based on the capacitance depends on the formation of an electric field in space.

Here, in the present invention, the mutual coupling occurring between the metal member 101 and the respective second electrodes 102b to 102e affects the resonance between the metal member 101 and the second electrodes 102b to 102e.

That is, the plurality of second electrodes 102b to 102e is arranged around the metal member 101, so that independent resonance points are caused by the mutual coupling between the metal member 101 and the respective second electrodes 102b to 102e, in addition to inherent resonance points between the second electrodes 102b to 102e, due to capacitance C caused by the mutual coupling between the metal member 101 and the second electrodes 102b to 102e and inherent inductance L of the metal member 101.

When the second electrodes 102b to 102e have different lengths and areas from each other, the mutual coupling of the respective second electrodes 102b to 102e and the metal member 101 is also different from each other. Therefore, the resonance points due to the mutual coupling between the metal member 101 and the second electrodes 102b to 102e are also different from each other.

When the inherent resonance points independent of each other increase as described above so that the partial discharge (PD) occurs in the transformer 10, it becomes possible to receive a signal of a frequency band that is wider than a frequency band due to the partial discharge.

That is, the frequency band of the partial discharge signal generated inside the transformer 10 is typically 0.5 to 1.5 GHz, which is an UHF band. In order to detect the signal of such frequency band, an electrode capable of detecting a signal of a wide band is necessary.

According to the present invention, a frequency signal of a wide band may be detected by increasing the number of the resonance points at the second electrodes 102b to 102e through the mutual coupling between the second electrodes 102b to 102e and the metal member 101.

In addition, according to the present invention, it is possible to improve the accuracy and reliability of internal defect detection by lowering a reflection loss at the second electrodes 102b to 102e due to such mutual coupling. That is, a large number of resonance points are generated as described above due to LC coupling between the metal member 101 and the second electrodes 102b to 102e, so that the reflection loss at the second electrodes 102b to 102e is lowered over the entire band. Herein, the fact that the reflection loss is lowered over the entire band means that the detection performance of the electrical signal is improved over the entire band.

As described above, according to the present invention, resonance occurs between the second electrodes 102b to 102e and resonance occurs due to mutual coupling between the second electrodes 102b to 102e and the metal member 101, whereby the reflection loss at the second electrodes 102b to 102e is lowered so that the detection performance of the electrical signal is improved, as well as a signal of a wide band frequency is detected.

An insulating member 103 is formed to include the metal member 101 and the plurality of electrodes 102. The insulating member 103 may be processed to be molded and cured in a state that the plurality of electrodes 102 are disposed around the metal member 101 at a predetermined distance, whereby the metal member 101 and the plurality of electrodes 102 are provided in such a manner to be inserted into the insulating member 103.

Accordingly, when the transformer internal defect detection apparatus 100 according to the present invention is inserted into the transformer 10 to detect the internal defects, the metal member 101 and the electrodes 102 are protected from other materials included in the transformer 10 so as to block the influence of the external environment while detecting the electrical signal at the electrode 102.

In another embodiment of the present invention, the transformer internal defect detection apparatus 100 may be configured to further include a gas sensor 104 provided at an end of the metal member 101.

The gas sensor 104 is provided at an end of the metal member 101 to detect gas existing inside the transformer 10. Since the internal defects of the transformer 10 are closely related to a hydrogen-based gas or a hydrogen mixture gas, the gas sensor 104 according to the present invention includes a hydrogen sensor. Of course, such gas sensor 104 may include various sensors in order to detect desired gases.

A cable for transmitting the detected signal is connected to the gas sensor 104, and a detection signal detected by the gas sensor 104 is transmitted through such a cable.

Herein, the gas sensor 104 according to the present invention may be provided inside the insulating member 103 or provided to be exposed to the outside of the insulating member 103 while being provided at an end of the metal member 101.

However, in order to accurately detect the gas existing in the transformer 10, it is preferable that the gas sensor 104 is provided to be exposed to the outside of the insulating member 103 while being provided at an end of the metal member 101

One of the important features of the present invention is the position of the gas sensor 104 relative to the plurality of electrodes 102 when the gas sensor 104 is provided at an end of the metal member 101.

Because the gas sensor 104 may affect an electric signal generated due to internal defects and received by each electrode 102 while detecting the gas existing in the transformer 10, it is important that the gas sensor is provided at a position where there is no or minimal effect on the electric signal.

That is, since the gas sensor 104 has a metal component therein and thus acts as capacitance together with the respective electrodes 102 to affect the detection performance due to the electrical signals received by the respective electrodes 102, the appropriate position must be determined to have no or minimal effect on the electrical signal.

In particular, in the present invention, the respective electrodes 102 are set all the same or differently from each other in characteristics such as length, area, and shape, so that it is necessary to set a point at which the effect on the electrical signal is minimized according to such characteristics.

Such characteristics of the respective electrodes 102 depend on characteristics of the transformer 10 to detect the internal defects, and therefore, the position of the electrode 102 should be set in consideration thereof.

Therefore, when the characteristics such as the length, the area, and the shape of the respective electrodes 102 are determined, it is important to determine the point at which the effect of the gas sensor 104 on the electrical signal at the respective electrodes 102 is minimized while continuously changing the occurrence position of the internal defects of the transformer 10 and the size and the scale of the internal defects are continuously changed. To this end, a simulation environment may be constructed so that the position may be determined by repetitive experiments through the simulation.

Thus, according to the present invention, the gas sensor 104 is preferably provided at an end of the metal member 101, which is the position at which the effect on the electrical signal at the each electrode 102 is minimized by performing such repetitive simulation. Herein since the position of the gas sensor 104 is also related to the length of the metal member 101, it is preferable to set the length of the metal member 101 according to the position at which the effect of the gas sensor 104 on the electrical signal at each electrode 102 is minimized. This should be determined depending on characteristics of the transformer 10, and length, shape, etc. of the electrode.

Meanwhile, the transformer internal defect detection apparatus 100 according to the present invention includes an analyzer 10 for receiving signals detected by the plurality of electrodes 102 and the gas sensor 104 to analyze the internal defects of the transformer 10. The connection of the analyzer 105 is shown in FIG. 2.

The analyzer 105 analyzes signals transmitted from the plurality of electrodes 102 and the gas sensor 104 through cables, respectively, to determine the internal defects. For example, it is determined whether a partial discharge (PD) is generated from an electrical signal detected by the plurality of electrodes 102, and a determination is made as to whether an electric or thermal fault has occurred from a signal detected from the gas sensor 104. To this end, the analyzer 105 is preferably provided with a program for determining the internal defects of the transformer from the received signal.

Figure 2:
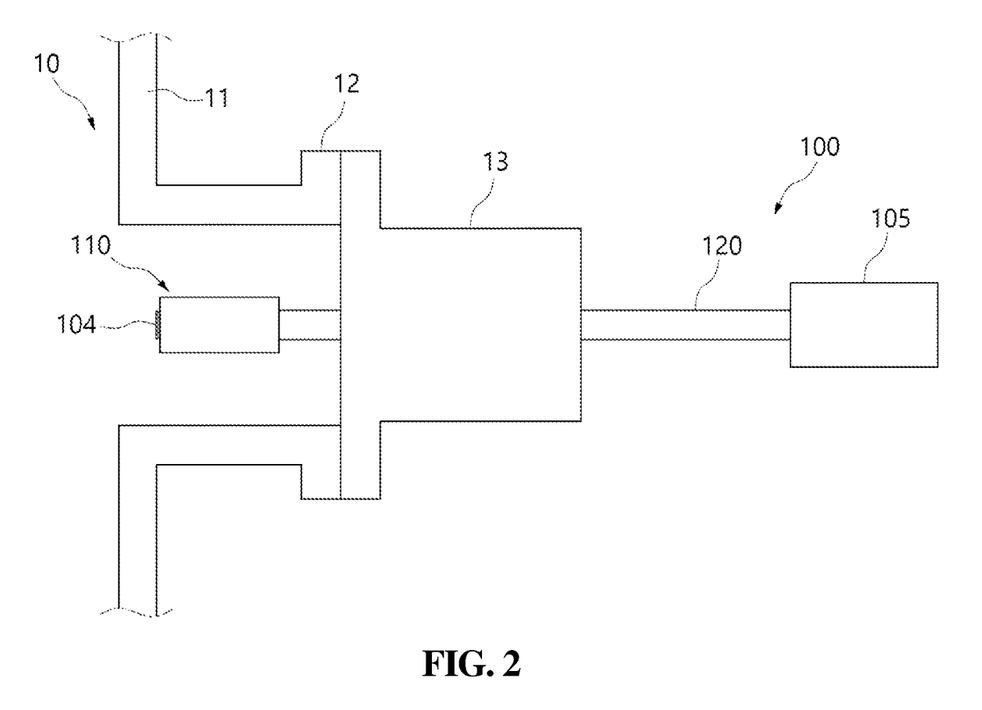
FIG. 2 is a diagram showing an example in which the transformer internal defect detection apparatus according to the present invention is provided inside a transformer.

FIG. 2 is a diagram showing an example in which the transformer internal defect detection apparatus according to the present invention is provided inside a transformer.

Referring to FIG. 2, in the transformer internal defect detection apparatus 100 according to the present invention, a sensor head unit 110 is provided, in which a metal member 101, a plurality of electrodes 102, an insulating member 103, and a gas sensor 104 are integrally combined, the sensor head unit 110 being connected to an end of an insulation support 120 having a predetermined length.

The sensor head unit 110 is inserted into the transformer 10 from the outside of the transformer 10 by the insulation support 120 so that the sensor head unit 110 is positioned inside the transformer 10.

Herein, the sensor head unit 110 is inserted into the transformer 10 through a drain valve 12 which is preferably provided in a part of an external tank 11 of the transformer 10 by the insulation support 120, and then sealed by a valve stopper 13.

Therefore, an electric signal and a gas detection signal generated due to the internal defects of the transformer 10 are detected by the plurality of electrodes 102 and the gas sensor 104 included in the sensor head unit 110 and then transmitted to an analyzer 105, which is present outside the transformer 10, through a cable (not shown).

The insulation support 120 may be implemented as a pipe having a space therein, and the cable may be connected to the electrode 102 and the gas sensor 104, respectively, through the inner space of the insulation support 120.

Figure 3A:
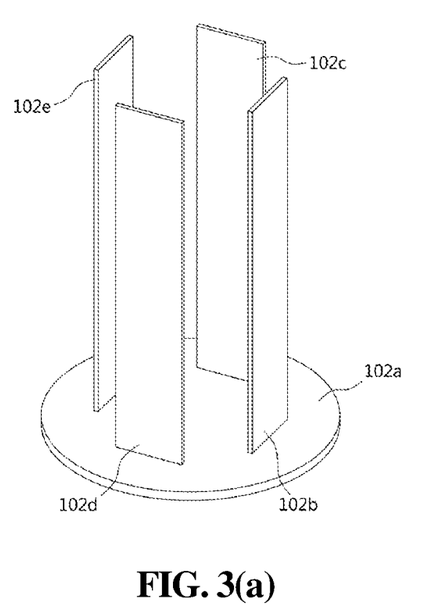
FIGS. 3(a) and 3(b) are exemplary views showing electrodes in a transformer internal defect detection apparatus according to an embodiment of the present invention.
Figure 3B:
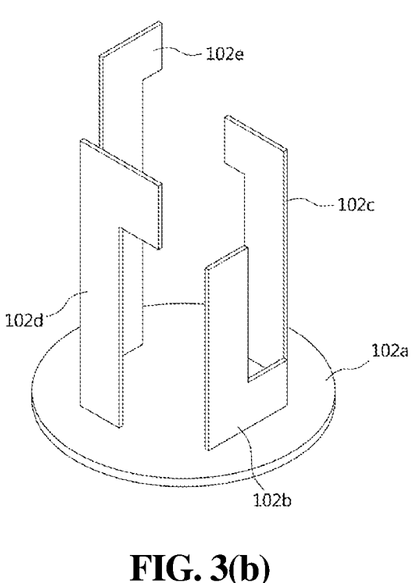

FIGS. 3(a) and 3(b) are exemplary views showing electrodes in a transformer internal defect detection apparatus according to an embodiment of the present invention.

Referring to FIGS. 3(a) and 3(b), a plurality of electrodes 102 according to the present invention includes a first electrode 102a connected to an end of a metal member 101 and other second electrodes 102b to 102e connected to the first electrode 102a to be provided in parallel with the metal electrode 101, respectively.

FIG. 3(a) shows an example in which the plurality of second electrodes 102b to 102e have the same shape, and FIG. 3(b) shows an example in which the plurality of second electrodes 102b to 102e have different shapes from each other.

This is to make the respective second electrodes 102b to 102e have mutual coupling characteristics different from that of the metal member 101.

The length, area, and shape of the second electrodes 102b to 102e may be variably determined depending on characteristics of the transformer internal defect detection apparatus 100 which is to be implemented and/or characteristics of the transformer 10 to detect the internal defects.

Figure 4:
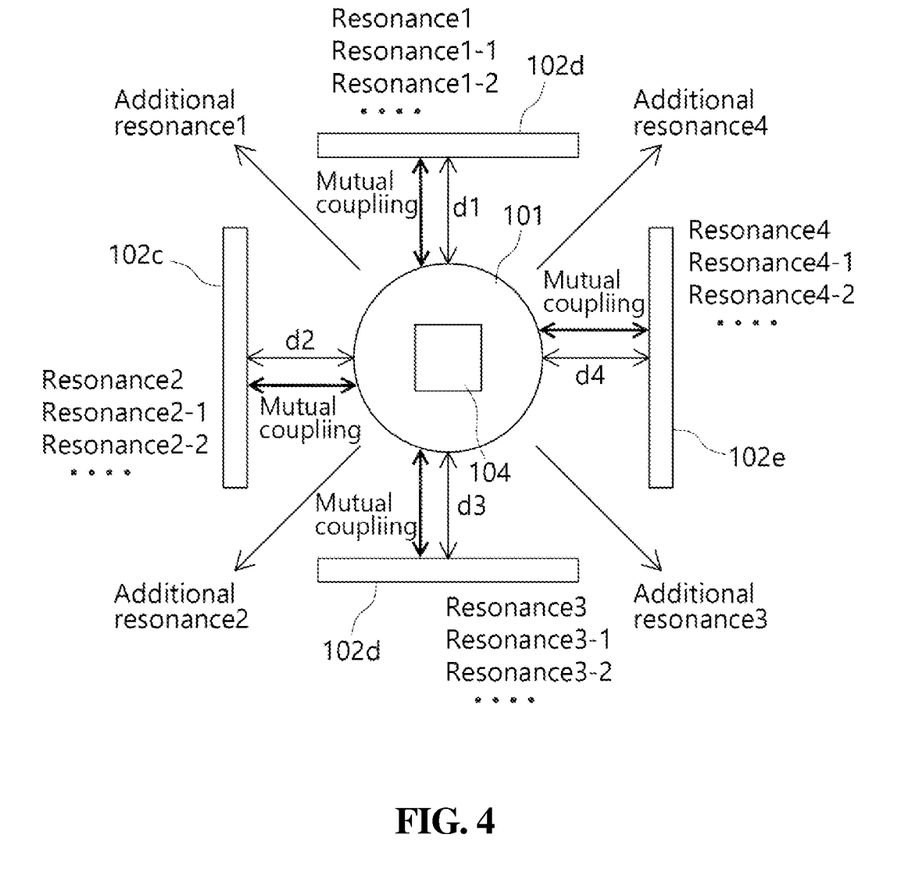
FIG. 4 is a view showing a resonance generation principle according to an interaction between a metal member and a plurality of electrodes in a transformer internal defect detection apparatus according to the present invention.

FIG. 4 is a view showing a resonance generation principle according to an interaction between a metal member and a plurality of electrodes in the transformer internal defect detection apparatus according to the present invention.

Referring to FIG. 4, the transformer internal defect detection apparatus 100 according to the present invention is configured to include the metal member 101 and the plurality of electrodes 102 inside the insulating member 103, as described above, and in particular, the metal member 101 and the plurality of second electrodes 102b to 120e are arranged parallel to each other with a predetermined distance therebetween.

It is preferable that distances d1 to d4 between the metal member 101 and the second electrodes 102b to 102e are set to such an extent that interaction may occur therebetween. These distances d1 to d4 are set differently depending on characteristics such as the length, area, and shape of the respective second electrodes 102b to 102e.

This is because the distance at which the interaction occurs varies depending on characteristics of the respective second electrodes 102b to 102e.

When an interaction effect occurs between the metal member 101 and the respective second electrodes 102b to 102e, additional resonance occurs between the metal member 101 and the respective second electrodes 102b to 102e, thereby reducing reflection loss.

This is because the number of resonance points in the respective electrodes 102b to 102e increase from one to a large number due to occurrence of additional resonance.

In addition, such additional resonance is generated so that the detection bandwidth in the respective electrodes 102b to 102e may be preferably expanded. As a result, it is possible to detect an electrical signal generated due to internal defects of the transformer 10 in a wide frequency band, thereby improving detection performance.

Furthermore, additional resonance points are generated between the respective electrodes 102b to 102e, whereby directionality for reception of the electrical signal may be also improved.

Figure 5A:
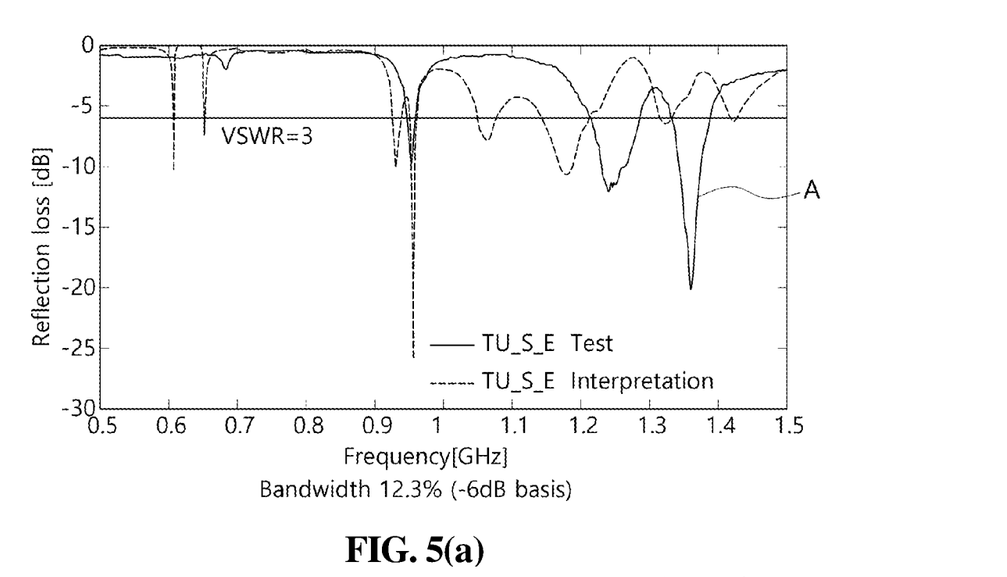
FIGS. 5(a) and 5(b) are graphs showing a comparison between a reflection loss when a transformer internal defect detection apparatus according to an embodiment of the present invention is applied and a reflection loss according to the related art.
Figure 5B:
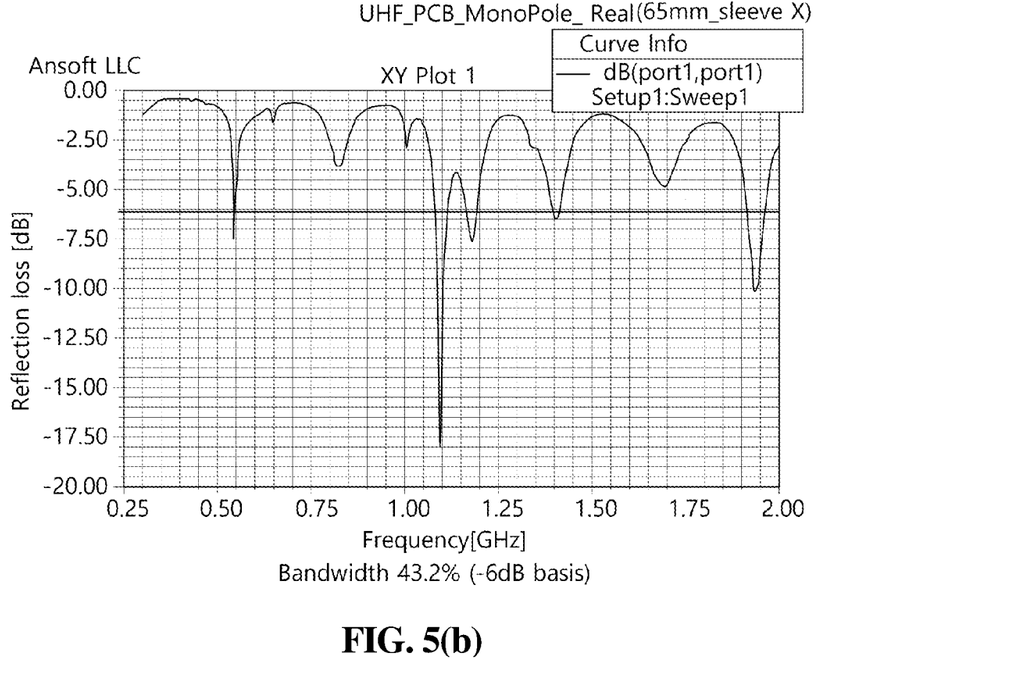

FIGS. 5(a) and 5(b) are graphs showing a comparison between a reflection loss when a transformer internal defect detection apparatus according to an embodiment of the present invention is applied and a reflection loss according to the related art.

Referring to FIGS. 5(a) and 5(b), a transformer internal defect detection apparatus 100 according to the present invention is such that a metal member 101 is inserted into an insulating member 103 and a plurality of electrodes 102 are disposed around the metal member 101.

It is experimentally shown that the number of the resonance points is increased by mutual coupling between the metal member 101 and the plurality of electrodes 102 and the reflection loss is improved due to the increase of the resonance points. The improvement in the reflection loss is confirmed when comparing such experimental result with the experimental result of the internal defect detection apparatus in the related art.

FIG. 5(a) is a graph of reflection loss according to the related art, and FIG. 5(b) is a graph of reflection loss according to the present invention.

The reflection loss graph in the related art is a result of an experiment which is performed based on a transformer internal defect detection apparatus disclosed in Korean Patent No. 1095778. That is, the reflection loss is measured when four electrodes having the same size and shape are attached to an insulating member.

Referring to the graph of FIG. 5(a) showing the experimental result of the related art, it may be seen that a total of four resonance points generated by a combination of L and C are generated on the solid line of the reflection loss indicated by A, which means that one resonance point is made by each of four electrodes.

On the other hand, referring to the graph of FIG. 5(b) according to the present invention, the solid line of the reflection loss indicated by B indicates that a large number of resonance points are generated due to all possible LC coupling and the reflection loss is lowered over the entire band. This means that the detection performance of the electrical signal is improved over the entire band because the reflection loss is lowered over the entire band.

As described above, the transformer internal defect detection apparatus 100 according to the present invention is such that the metal member 101 is inserted into the insulating member 103 and the plurality of electrodes 102 is arranged around the metal member 101, whereby the number of resonance points is increased due to the mutual coupling between the metal member 101 and the plurality of electrodes 102, thereby improving the detection performance of the signal caused by a fault of the transformer.

In addition, the transformer internal defect detection apparatus 100 according to the present invention further includes a gas sensor 104 for detecting the internal gas of the transformer 10 at an end of the metal member 101 so that the plurality of electrodes 102 and the gas sensor 104 may be integrally combined into a single module, whereby electrical signals for the internal defects of the transformer and gas contained in the insulating oil inside the transformer may be detected at the same time.

Herein, upon determining the position of the gas sensor 104, the position of the gas sensor 104 is set such that the effect on the electrical signal received by the plurality of electrodes 102 is minimized, thereby improving the detection performance of the gas sensor 104.

While the present invention has been described in connection with what is presently considered to be the most practical and preferred embodiment, it is to be understood that the invention is not limited to the disclosed embodiments. That is, within the scope of the present invention, one or more of all of the elements may be selectively coupled to each other. It is to be understood that the terms "includes", "comprises", or "having", as used herein, mean that a component can be implied unless specifically stated to the contrary, but should be construed as including other elements. All terms including technical or scientific terms have the same meaning as commonly understood by one of ordinary skill in the art to which this invention belongs, unless otherwise defined. Terms commonly used, such as predefined terms, should be interpreted to be consistent with the contextual meanings of the related art, and are not to be construed as ideal or overly formal, unless expressly defined to the contrary.

While the present invention has been described in connection with what is presently considered to be practical exemplary embodiments, it is to be understood that the invention is not limited to the disclosed embodiments. On the contrary, is intended to cover various modifications and equivalent arrangements included within the spirit and scope of the appended claims. Therefore, the embodiments disclosed in the present invention are not intended to limit the scope of the present invention but to limit the scope of the technical idea of the present invention. The scope of protection of the present invention should be construed according to the following claims, and all technical ideas within the scope of equivalents thereof should be construed as being included in the scope of the present invention.

The invention claimed is:

1. An apparatus for detecting internal defects in a transformer, the apparatus comprising:
   a metal member having a predetermined length;
   a plurality of electrodes provided around the metal member to detect electric signals generated due to the internal defects of the transformer; and
   an insulating member,
   wherein the metal member and the plurality of electrodes are disposed inside the insulating member, and
   wherein the insulating member surrounds the metal member and the plurality of electrodes from outside.

2. The apparatus of claim 1, wherein a first electrode of the plurality of electrodes is provided to be in contact with an end of the metal member.

3. The apparatus of claim 2, wherein the remaining electrodes except the first electrode of the plurality of electrodes are connected to the first electrode to be provided in parallel to the metal member.

4. The apparatus of claim 3, wherein the remaining electrodes are each implemented in a shape of a plate having a predetermined area.

5. The apparatus of claim 3, wherein the metal member has a cylindrical shape, and the remaining electrodes are each disposed such that inner surfaces thereof are parallel to an outer surface of the cylindrical metal member while having a predetermined area.

6. The apparatus of claim 5, wherein the remaining electrodes each have a length, an area, and a shape different from each other.

7. The apparatus of claim 6, wherein the remaining electrodes are provided at a distance at which mutual coupling of each with the metal member occurs.

8. The apparatus of claim 7, wherein the remaining electrodes each generate resonance different from the metal member.

9. The apparatus of claim 1, further comprising:
a gas sensor provided at an end of the metal member to detect gas dissolved in insulating oil inside the transformer.

10. The apparatus of claim 9, wherein the gas sensor is provided at the end of the metal member so as to be exposed to outside the insulating member.

11. The apparatus of claim 9, wherein the gas sensor is provided at a position at which an effect on an electrical signal received by the plurality of electrodes is minimized.

12. The apparatus of claim 9, wherein the gas sensor includes a hydrogen detection sensor for detecting hydrogen gas of the dissolved oil inside the transformer.

13. The apparatus of claim 9, wherein the metal member, the plurality of electrodes, the insulating member, and the gas sensor are integrally combined to constitute a sensor head unit, and the sensor head unit is connected to an end of an insulation support having a predetermined length and thus inserted into the transformer from an outside of the transformer.

14. The apparatus of claim 9, further comprising:
an analyzer receiving signals detected by the plurality of electrodes and the gas sensor to analyze the internal defects of the transformer.

15. An apparatus for detecting internal defects in a transformer, the apparatus comprising:
a metal member having a predetermined length;
a plurality of electrodes provided around the metal member to detect electric signals generated due to the internal defects of the transformer; and
an insulating member, wherein the metal member and the plurality of electrodes are disposed inside the insulating member; and
a gas sensor provided at an end of the metal member to detect gas dissolved in insulating oil inside the transformer,
wherein the metal member, the plurality of electrodes, the insulating member, and the gas sensor are integrally combined to constitute a sensor head unit, and the sensor head unit is connected to an end of an insulation support having a predetermined length and thus inserted into the transformer from an outside of the transformer.

* * * * *